United States Patent [19]

Weissman et al.

[11] Patent Number: 5,602,674

[45] Date of Patent: Feb. 11, 1997

[54] COMPUTERIZED SPECIMEN ENCODER

[75] Inventors: Mark Weissman, Wayland; Louis Kamentsky, Cambridge; Lee D. Kamentsky, Arlington, all of Mass.

[73] Assignee: Compucyte Corp., Cambridge, Mass.

[21] Appl. No.: 491,414

[22] Filed: Jun. 16, 1995

Related U.S. Application Data

[63] Continuation-in-part of Ser. No. 89,243, Jul. 9, 1993.

[51] Int. Cl.$^6$ .......................... G02B 21/26; G02B 21/34; G01J 1/20; H04N 7/18
[52] U.S. Cl. .......................... 359/393; 359/396; 359/397; 250/201.3; 250/201.8
[58] Field of Search .................................. 359/391, 393, 359/396, 397; 250/201.3, 201.8

[56] References Cited

U.S. PATENT DOCUMENTS

| | | | |
|---|---|---|---|
| 4,513,438 | 4/1985 | Graham et al. | 382/6 |
| 4,810,869 | 3/1989 | Yabe et al. | 250/201 |
| 4,965,725 | 10/1990 | Rutenberg | 364/413.1 |
| 5,009,503 | 4/1991 | Murphy et al. | 356/339 |
| 5,038,035 | 8/1991 | Nishimura et al. | 250/311 |
| 5,073,857 | 12/1991 | Peters et al. | 364/413.1 |
| 5,257,182 | 10/1993 | Luck et al. | 364/413.1 |
| 5,260,825 | 11/1993 | Nagano et al. | 359/368 |
| 5,276,550 | 1/1994 | Kojima | 359/368 |
| 5,287,272 | 2/1994 | Rutenberg et al. | 364/413.1 |

Primary Examiner—Timothy P. Callahan
Assistant Examiner—T. Lam
Attorney, Agent, or Firm—Graham & James LLP

[57] ABSTRACT

A computerized specimen encoder for use with microscope analysis and pathological studies. The slide encoder is attached to the movable microscope stage, whereby X-Y plane movement and location, is correlated to examination of a specimen on an identified slide, with information marking and location being directly correspondingly written on computer storage media, during the examination. The information marking is in the form of computer generated indicia which are placed at a computer image location of the slide at predetermined time intervals. Subsequent use of the computer-stored information, coupled with the slide encoder, in a slide re-examination, permits independent retrieval of such information and location on the slide. The encoder device is provided with a grayscale marker which marks in varying shades of gray, ranging from white to black, the time spent by a slide screener on a particular portion of the specimen and the number of times spent viewing a particular portion of the specimen.

11 Claims, 2 Drawing Sheets

COMPUTERIZED SPECIMEN ENCODER

This is a continuation-in-part of co-pending application Ser. No. 08/089,243, filed Jul. 9, 1993.

Field of the Invention

This invention relates to computerized location marking of information on microscope specimens such as on microscope slides, with particular utility in pathological examination and re-examination of the slides.

BACKGROUND OF THE INVENTION

Specimen slides such as Pap smears are examined by microscope users for specific types of events such as cancer cells. These events are, however, relatively rare and once found are difficult to re-locate for confirmation by others. This is a severe drawback, since an important requirement for cancer screening laboratories is certification by a pathologist, with the need for independent relocation and verification.

Another serious concern with the quality of slide screening, is the nature of the original screening, with a current lack of a positive check on the capability of the screener, and even a lack of quality control feedback for even the most skilled screener. This can and has led to unnecessary deaths, and liability, by reason of missed cell anomalies, resulting in delayed or missed treatment. No reliable and certainly no economical system currently exists for providing requisite slide screening checks as well as checks on screener capability or even a system which provides a quality control feedback to users. The lack of quality control feedback causes even the most skilled screener to operate in a vacuum, without knowledge of what provides proper results in a particular mode of screening.

Methods for re-screening slides are either very crude or entail great economic expense. The prevailing method in aiding relocation is the placement of an ink dot on the slide near the location of the event. This method has proven to be crude, awkward, time consuming and inaccurate. In addition, with this method, it is not possible to ascertain if the entire specimen area of the slide has been uniformly examined or if the areas of the specimen have or have not been scanned. It is accordingly often the case, that if the user is interrupted, it is necessary to restart slide examination. With microscope examination of items, such as diamonds or other types of jewels, for identifying characteristics, the use of ink dots can actually detrimentally mar the appearance of the item.

Ink dot marking and other similar location methods also do not provide any information at all regarding the rate of examination, or time spent at a particular area (important quality control factors). The dots merely function as markers and cannot provide a description of the event or provide any scan history record. As a result of the realization that cancer screening is inaccurate, because areas are missed, there is a major effort underway to improve the quality of screening laboratories by requiring re-screening of randomly selected slides.

Prior art automated screening devices, in the form of motor controlled stage or slide holder devices, generally provide a visible indicia on a slide for observation by the user with coordinates set into the device. The slide is moved in a meander pattern until an event of interest is discovered, at which point the slide is stopped and the position is recorded. While this provides both recording of position and a recording of scan history, it is limited by the need for the user to wait until the event comes into the field of view to stop the meander, rather than by controlling movement by hand. Such devices, besides being very expensive, also interfere with normal use of the microscope and the motion control devices thereof detract from the feel of a normal microscope stage positioning control. Often this detracts from the attention required from the examining screener and a screener can readily "fall asleep" at the lens. Thus, while the physical movement of the screening has been automated, the actual mental assimilation of what is being screened in fact deteriorates.

Very recently, a new device has been developed which utilizes personal computers to record slide data. This device, with video input to specially modified microscopes, superimposes the display of a computer output on the microscope field for viewing by the user. A mouse is used to mark off events of interest. The device is described in *Cytometry*, vol. 13, pages 109–166 (1992) and *Analytical & Quantitative Cytology & Histology*, vol. 14, August 1992 and is the basis for the currently marketed HOME device. While useful, such devices are inherently expensive and complex in requiring extensive modification of microscopes (i.e., only HOME supplied microscopes are operative with the system) thereby limiting their utility with respect to different field-available microscopes. As a result, widespread reviewing capability (for both reasons of economics and availability) is severely restricted.

In parent application, Ser. No. 08/089,243 (the disclosure thereof being included herein by reference thereto), the invention therein is described as comprising an economical method end device for use during microscope examination and qualitative control of re-screening of specimens, particularly of specimen slides. The method and device described therein, involve encoding the varying viewing positions on the specimen to correlative computer pixel locations represented by indicia, such as dots, generated by the computer, at pre-selected time intervals. Dots (the exemplified marking indicia), representing varying fields of view, are in turn marked with numbers or symbols indicative of degree of interest of events within the field. Encoding is effected by a mouse or other similar type of encoder which correlates viewing position to specifically correlated location on a screen (as retrieved from computer recordation storage). Retrieval is then easily effected on rescreening by placing the cursor of the computer on a marked event of interest on the screen, by means of movement of the microscope stage, which thereby correlatively positions the lens directly on the event of interest. The area of interest is thus directly viewable under the microscope. A voice record associated with the event may also be made or retrieved in this manner.

In accordance with the method of the parent application, the computer is instructed to and generates time controlled markings, such as dots, which correlate to slide viewing areas on the representative slide image. For example, at time intervals of one second, as regulated by the internal clock of the computer, a dot is generated as being representative of the full area being viewed at that time. As a result, with a subsequent review of the slide, there is a specific correlation of the computer stored dot notation on the representative slide image, directly with an actual original viewed area of the slide. It is thereby also readily ascertainable which areas have and have not been viewed as a function of total specimen area.

A further very useful quality control feature is that the density of dots is a direct indication of the rate at which the slide had been examined. Thus, closely spaced dots indicate a slow scan and widely dispersed dots indicate a more rapid scan.

With the generation of marks, such as dots, each mark (e.g. dot) is further capable of being labelled in turn, such as with a numerical grading, alpha abbreviation, descriptive symbol (predesignated icon) and the like, to inform a reviewer of location of specific events on the examined specimen and their relative importance and/or nature. If desired, a digitized voice record describing the particular events being labelled may also be generated and stored for correlative retrieval upon review of the slide.

In addition to the aforementioned quality control information, it is very useful to also know on a day-to-day and slide-by-slide basis that the slide reviewer or screener is actually giving each specimen "adequate coverage" to locate rare events.

For quality control purposes, "adequate coverage" involves separate parameters of temporal and spatial coverage, but the most useful parameter is a function of both time and space combined. Specifically, it may be useful, but not sufficient, as a measure of screening quality, to (a) record that "x" number of minutes were spent screening a slide, or (b) show that a certain area of the specimen was or was not screened, or even (c) that "y" seconds were spent with the microscope stage at a certain location (factors which were described as being determined by means of the invention of said parent application).

Though these factors may, in and of themselves, give some indication of screening performance, they are of limited value because many minutes may be spent on a small area of the specimen to the exclusion of large areas of possible interest, thus negating the value of the overall length of time spent in reviewing the slide. Furthermore, even a showing that a certain area of the specimen fell under the screener's view does not provide the necessary information that sufficient time was spent looking at that location, to enable a qualified screener to recognize objects or cells of interest.

The manner in which the invention of the parent application is concerned with the laying down of dots as a representation of the field of view in a time-dependent fashion does not however take into account the fact that during rapid screening of a specimen, the amount of time available for viewing any object in the field of view is partly a function of the distance of that object from the center of the field of view. Objects or cells near the outside of the field of view will be seen for only a fraction of the time that cells passing through the center of the field of view are seen. This is based on a screening pattern which is a rapid series of jumps and stops, which constitutes common screening technique, as described in published studies. To compensate for this problem in viewing outlying cells, operators are supposed to screen in overlapping rows or columns (depending upon the screener's preference of movement) so that cells near the outside of the field of view, on one pass of the microscope, get a second chance to be inspected.

SUMMARY OF THE INVENTION

Generally the present invention comprises a method and a device for effecting said method. The device comprises an improvement of the device described in said parent application, as described above, wherein the device further comprises means for measuring elapsed time of screening a specimen by a screener, and means for calculating overall coverage of the screening relative to the slide sample, i.e., the percentage of the specimen screened, (a) as a fraction of the entire specimen or (b) as a fraction of a region of the specimen defined by the smallest rectangle or circle that encloses points that have been viewed.

The aforementioned percentage, as a fraction of the entire specimen, is useful for disciplines such as Pap screening in which the entire specimen is supposed to be viewed. The percentage, as a fraction of a region of the specimen defined by the smallest rectangle or circles enclosing points that have been viewed, is useful for evaluating coverage of other specimens which do not cover the entire slide, for example, so called Thin Prep® specimens in which cells are deposited in a circular pattern on a slide.

Means are provided, in accordance with the present invention for displaying via a grayscale, the dwell time at each location (or pixel of the computer representative image), whereby during rapid screening, the central area of the moving circular cursor (as described in the preferred embodiment of the parent application) that sweeps out a track on the screen, is darker than the edges of the field of view. As a screener overlaps the column or row on the next pass, the time spent on the overlapping edges is added, and the edges darken to indicate additional inspection time. Conversely, if there is no overlapping of fields and the screener moves at too rapid a pace, the visual display shows a significant amount of light gray areas (in the lower end of the gray scale) to a reviewer of the initial screening.

Based on variations in the grayscale, the device further preferably comprises means which computes the percentage of overlapping fields. This measurement is a useful measure of screening performance which screeners and screening reviewers can use to refine performance, i.e., too little overlap can lead to false negative findings, while too much overlap indicates inefficient performance.

In actual practice, using the device of the present invention, a supervisor reviewing the performance of a cytotech, can call up a list of specimens that were screened. The call up will include the elapsed time, percent of coverage, and percent of overlap indicated for each one. It is then possible to rank-order the specimens in terms of least time, least coverage, or least overlap. The supervisor is then able to selectively review the gray scale screening pattern for any specimen that may appear to have received less than optimal attention.

This quality control procedure and device provides a supervisor with a rational and efficient method for choosing which specimens to review for teaching and quality control purposes, in contrast to the present method of randomly selecting a percentage of slides for review, a mathematically demonstrated pointless procedure with respect to searching for rare events.

It is therefore an object of the present invention to provide a specimen encoding device for a microscope, which provides a measurement of elapsed time of screening a specimen.

It is a further object of the present invention to provide means for calculating overall coverage or percentage of the specimen screened.

It is yet another object of the present invention to display by means of a varying "gray" scale, the dwell time of screening at each location on the specimen.

It is still another object of the present invention to provide a device which computes percentage of overlapping of screened specimen segments.

These and other objects features and advantages of the present invention will become more evident from the following discussion and drawings in which:

SHORT DESCRIPTION OF THE DRAWINGS

DETAILED DESCRIPTION OF THE INVENTION

Figure 1:
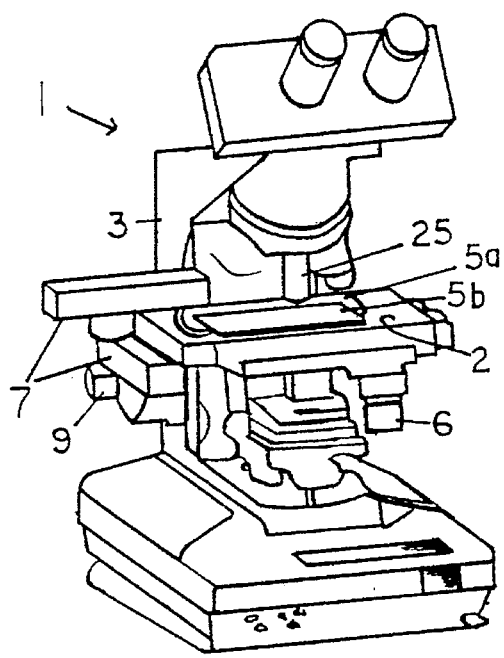
FIG. 1 is an isometric view of a microscope with an embodiment described in the parent application and used in the present invention, in the form of a position encoder affixed to the movable microscope stage.
Figure 1:
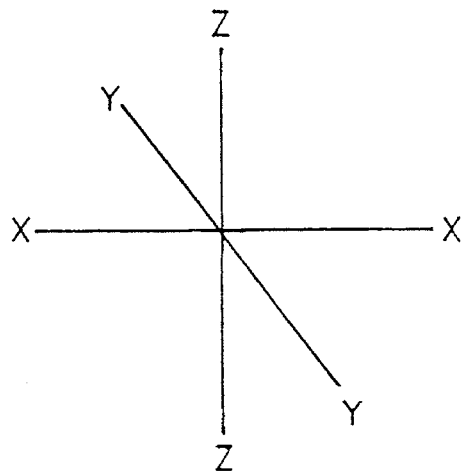

Method and Operation of Device in Parent Application

In accordance with the method of the invention in the parent application, scanning examination of a microscope specimen is effected in the following manner:

1) operatively linking a computer, with a movable slide stage of a microscope, to correlatively record movement of the slide stage and a specimen thereon (e.g., a specimen carried on a slide), in the x-y plane in which the slide stage and specimen are movable;

2) fixedly placing an identified specimen on the movable stage;

3) moving the stage, with concomitant specimen movement, until the microscope viewing area is fixed on a predetermined starting location point of the cover slip, e.g., at the upper left hand corner of a slide carrying the specimen;

4) initiating correlative start location by the computer, to record subsequent movement in the plane in which the stage and specimen are movable;

5) moving the stage, with concomitant specimen movement, away from the starting location point, with microscope examination of the specimen at various locations thereon, with the linked computer recording such motion and the various viewing locations on computer storage medium;

6) causing the computer to automatically record, on the computer storage medium, indicia (such as black dots), at pre-determined time intervals, with said indicia correlating to the microscope viewing area location on the specimen, at the pre-determined time intervals; and 7) marking particular "indicia of interest" (sites corresponding to particular indicia, such as dots) with a distinguishing marking for subsequent retrieval and recognition.

The marking of the indicia of interest is either in the form of a recognizable alpha notation, symbol, or numerical grade, indicating its character and/or relative degree of importance or the indicia is marked with a digitized voice or audio record, describing the characteristics or importance of the area being so marked. The particular indicia can be so marked at any time during specimen examination or subsequent review.

With re-examination of the specimen, the specimen is placed on any similarly equipped microscope specimen stage (review is however independent of the type of microscope being used). The recording of the particular identified slide is recovered from the computer storage medium to a viewing screen. A cursor on the viewing screen provides a continual correlation of position thereon to the actual microscope viewing area. Movement of the microscope stage causes concomitant movement of the cursor. As a result, the cursor can be made to fall on a selected marked indicia which correlates to the area of interest on the specimen which was so marked. Such area can then be directly viewed, or any audio record can be played.

The density of marked indicia on the viewing screen provides an indication of the rate at which the specimen was originally examined. The denser the indicia, the slower and presumably the more careful the original examination. Absence of indica in a particular area of the specimen is indicative of such area not having been originally scanned and examined.

Method and Operation of the Present Invention

Generally the present invention comprises a computer specimen correlative encoder device, for use during examination and subsequent review of the examination, of a specimen with a microscope, essentially as described in said parent application, wherein during the examination and review of examination, the specimen is movably mounted relative to a viewing lens of the microscope; whereby the specimen is movable in an x-y direction plane, during said examination and review of examination. The encoder device comprises, in conjunction with a computer and a viewing screen:

a. correlation means for translating movement of the mounted specimen, in the x-y direction plane, to retrievable corresponding computer pixel locations and cursor movement on said viewing screen within a computer generated framed area diagram which correlatively contains the specimen;

b. means for marking microscope viewing areas, which are viewed during said examination, as correlated to the computer pixel locations, on the viewing screen and within the computer generated framed area diagram, with computer generated marking indicia.

The present invention is characterized by the additional element of:

c. means for recognizably varying the computer generated marking indicia, corresponding to specifically viewed microscope viewing areas, as a function of time spent viewing each of said viewing areas and/or as a function of the number of times each, or a portion of each, of said viewing areas has been viewed.

Thus, in a further method step of the present invention, visible measurement of viewing dwell time is effected and displayed on screen for review.

The device further comprises means for tagging, with predetermined symbols, numbers, letters, icons, etc., areas of the viewing screen, correlating to areas of the specimen, which are of interest, for subsequent review and said means for tagging further provides an indication of the degree of relative interest and/or type of interest.

In a preferred embodiment, the device further comprises means for viewing the tagging symbols, separate from said marking indicia. The screen, with multiple marking which indicates the areas examined, is replaced with an uncluttered screen showing only marked off areas of interest.

In a further useful embodiment the means for recognizably varying the computer generated marking indicia, further comprises means for recognizably varying portions of the marked indicia, corresponding to a selected viewed viewing area, as a function of distance from the center of the selected viewed viewing area.

In a highly preferred embodiment the device of the present invention comprises means for generating indicia with appearance falling on a gray scale, having predetermined shading variations of gray, ranging from white to black; wherein the predetermined variations in shades of gray, are correlated to:

a. preselected amounts of time spent in viewing a microscope viewing area;

b. the number of times a viewing area, or portion thereof, was viewed; or c. the distance a portion of a viewing area is relative to the center of the viewing area; and d. combinations of the preselected amounts of time, number of times and distance.

As a quality control feature of the present invention, the device, used during examination and subsequent review of the examination, of a specimen with a microscope, in accordance with the present invention, wherein a specimen is movably mounted relative to a viewing lens of the microscope in an x-y direction plane; comprises, in conjunction with a computer:

a. correlation means for translating movement of the mounted specimen, in the x-y direction plane, to retrievable corresponding computer pixel locations;

b. means for determining the area of the specimen viewed with the microscope during said examination, relative to the total area of the specimen viewable by the microscope. It is further preferred that means be provided for determining the area viewed at least twice during said examination, relative to the total area of the specimen viewed with the microscope during the examination.

Thus, in accordance with the present invention, additional feedback and information regarding the character of the original search, is obtained, wherein means are provided for an additional measure of accuracy in determining time spent by the screener at different areas of the specimen and a weighted scale of the quality of the screening.

The indicia generated by the computer, as described, is in the form of a grayscale track. Each time a particular area of the specimen is viewed, an additional shade of gray is added such that areas not scanned are designated as white. Dwell time can be custom set to change grayscale values ranging from white to black.

It is understood that the degree and amounts of gray increments are optional and may vary, as desired, for increased informativeness regarding dwell time per pixel. In fact any means for differentiation may be utilized, e.g., varying colors, etc. though shades or grey are more readily visually understood on a comparison basis.

In a preferred embodiment the grayscale track is represented as a two dimensional array of words. The array has a width of 544 elements and a height of 256 elements and a word size of five bits, thereby being capable of holding values of 0 to 3. The radius of the microscope visual field is determined during calibration and is converted into units of the array. At the beginning of the screening, all of the array elements are initialized to zero. During screening, the encoding device keeps track of the center of the microscope view field relative to the specimen and relates the position of the center of the view to the array to obtain an array index. The encoder is software controlled to determine which array elements correspond to portions of the specimen that are visible through the microscope by determining which elements are at a distance from the center that is less than or equal to the previously determined radius; those array elements within the radius correspond to visible areas of the microscope. The elements of the array are incremented under one of two conditions. Incrementation occurs to whatever area happens to be visible at the beginning of every second (time unit) and the area under the view is incremented whenever the stage coordinates change. The incrementation consists of adding one to each visible element in the array. The grayscale track is displayed by use of three threshold values: $T_{LightGray}$, $T_{DarkGray}$, and $T_{Black}$. Each array element is evaluated based on these three threshold values. If the array element's value is less than $T_{LightGray}$, it appears on the view screen as white, otherwise if the value is less than $T_{DarkGray}$, it appears as light gray, if the value is less than $T_{Black}$, it appears as dark gray. Higher values appear as black. By making the threshold values variable, it enables the view screen display to be customized for screeners of different skill levels.

In a preferred embodiment of the present invention, means are provided for measuring elapsed time spent screening the specimen while taking into account the possibility that the screener may interrupt the screening process to undertake some other task. An internal clock in the device keeps track of time spent between movements of the stage, at, while also maintaining an elapsed time $t_{total}$. Each time the user moves the stage, At is added to $t_{total}$ unless At is greater than $t_{interruption}$, a pre-set constant such as 60 seconds. With such elapsed time of non-motion (or more), at is reset to zero. Thus, $t_{total}$ is the actual total time spent screening the specimen, excepting those times when the screener interrupted scanning for more than the pre-set constant, $t_{interruption}$.

In displaying the extent of the initial screening (or any other screening which is monitored by the device) the view screen preferably displays the percentage of the slide screen by the user in a format of two different numbers. The first is the percentage of the specimen covered as a fraction of the total area of the specimen. The other is the percent of the specimen covered as a fraction of the smallest rectangle (or circle, where applicable, for specimens such as Thin Prep® slides wherein cells are deposited in a circular pattern) that encloses points within the specimen that have been viewed. These establish a threshold for values of an array element.

As an important part of the display, for quality control purposes, there is a depiction and read-out of the percent overlap of a specimen screening. This follows the normal screening technique, wherein the user screens the specimen by moving the stage, typically from left to right, to view a horizontal strip of the specimen, and then the user moves the stage slightly, up or down, and then from right to left, to view another horizontal strip. Alternatively, some users follow an up-down pattern to screen vertical strips. In order to guarantee that areas at the edge of the microscope view are examined as thoroughly as the center areas of the microscope view, screeners overlap adjacent strips and it is this overlap which is analyzed and depicted by the device of the present invention.

In one embodiment, overlap is calculated by comparing a new position with the previous position approximately 18 times per second. In each new position, the number of pixels which were not visible in the previous position's field of view is calculated. These are the new pixels in the new position (new field of view). Of these new pixels, the number which have been seen before is also calculated. These are the previously seen new pixels.

At each new position, if the previously seen new pixels comprise note than 70% of the new pixels, it is assumed that the operator is going back over previously viewed material and the numbers are discarded. Otherwise the new pixels and the previously seen new pixels are added to separate counters. The overlap is the total previously seen new pixels divided by the total seen pixels and converted into a percentage.

The device of the present invention optionally comprises means for making it capable of various useful measurement functions. Specifically, the device can be used to measure the distance between two points and the area enclosed by an arbitrary polygon.

In order to measure the distance between two points, the user initially positions the microscope stage so that a first point is visible at the center of the microscope's field of view. The user activates the device which records the x-y coordinates at that point. The user repeats the recordation of x-y coordinates at a second point of the microscope's field of view. With software instructions, the device subtracts the current x and y microscope stage coordinates from the previously recorded coordinates and squares the two differences, adds them, and takes the square root to determine the distance between the two points (in accordance with the Pythagorean theorem).

For area measurement, the user defines line segments of a polygon which encloses the specimen whose area is to be determined. To effect the area measurements, the user positions the microscope stage so that the center of the view area rests at points at the edge of the specimen. The user then traces the specimen in a clockwise or counter clockwise direction while recording representative edge positions. The area of the specimens is then determined by calculation of the sides of a rectangle which bounds the polygon. The device, with software instructions using a line crossing calculation technique, determines which areas of the rectangle are within the polygon and which lie outside the polygon. Substraction of the area of the latter from the area of the rectangle provides the area of the polygon and thus the area of the sample.

It is understood that the present method and device are applicable to microscope specimen examination in fields other than pathological determinations, such as metal stress analysis, fingerprint analysis, etc. in which areas or events of interest are marked for subsequent review. The present method and device are also applicable to microscope examination of specimens which do not require a slide carrier, but which are fixed into position, such as with a clamp, in replicable positions. For example, identification examination and reexamination of diamonds or other gems is possible with separate x-y plane examination of the various facets for specifically located identification markings. Similarly any three dimensional object, e.g. semiconductor chips, of appropriate dimensions, can be examined and reexamined for "events of interest" in each/or any number of its surface planes.

DETAILED DESCRIPTION OF THE DRAWINGS AND THE PREFERRED EMBODIMENT

With specific reference to the drawings, in FIG. 1, a typical microscope 1 (Olympus BH-2), is shown with a slide stage 2, movable in the x-y plane shown, mounted on relatively fixed frame 3. Slide 5b, with pathological specimen to be examined, is located and fixed into position on slide stage 2, with slide holder 5a. In operation, focus control knob 9 causes frame member 3 to move in the z-direction (up and down) for focussing relative to selected lens 25. At the point of proper focus, frame 3 is fixed in position and slide stage 2 moved in the x-y direction (the two dimensional viewing area of slide 5b) for full scanning of the pathological sample on slide 5b. Concentric knob control 6 is geared to effect such x-y direction movement.

Figure 2:
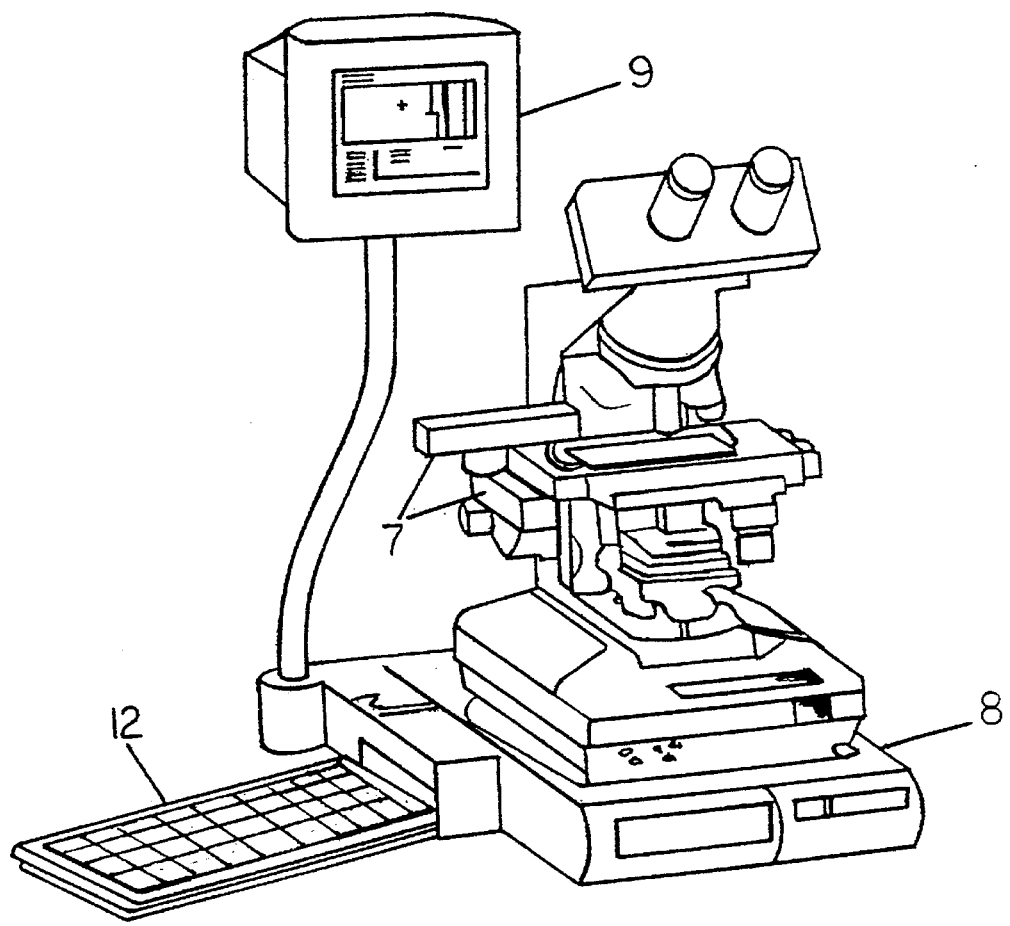
FIG. 2 is a representative view of a computer device, with viewing screen and storage capability, having marking controls, voice input and retrieval review, which is used to monitor specimens with computer correlative information and to provide markings and specimen scanning history.

A position encoder 7 is affixed, to slide stage 2, whereby an integrated circuit chip in the encoder provides a sequence of bytes encoding this motion through connection to computer 8. Software in the computer's operating system converts these signals into the computer display screen's (9) cursor position such as shown as a "+" in FIG. 2.

Figure 3A:
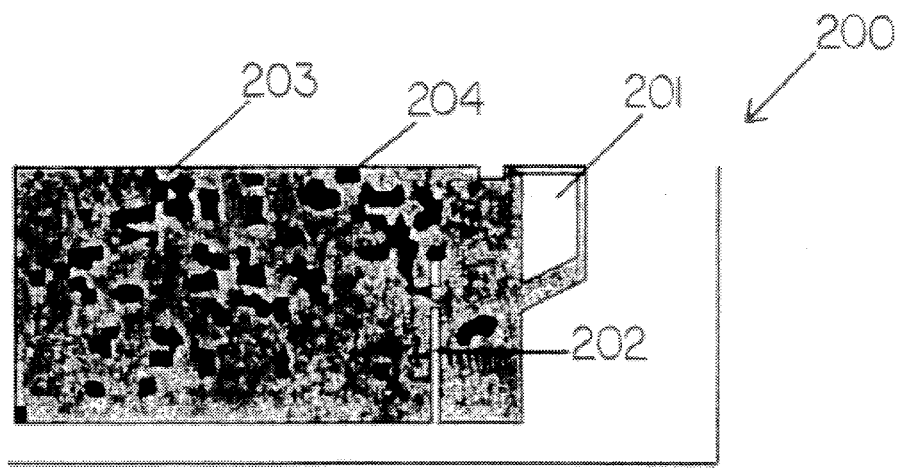
FIG. 3a depicts the computer screen representation of the examination of a specimen showing various areas of gray scale intensity ranging from white to black indicating the degree of scanning time and overlapping of scanning.
Figure 3B:
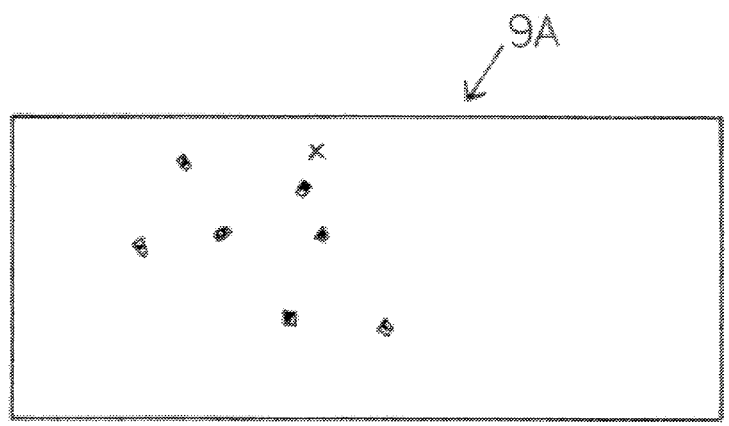
FIG. 3b depicts the screen of FIG. 3a, toggled to remove the grayscale history and to display only the events of interest, as marked with icons.

With reference to the computerized slide image 200 on screen 9 (showing representations of areas initially scanned) in Figure 3a, the image is indicative of an initial up-down scanning and overlapping patterns. White areas 201 are indicative of portions of the slide not scanned, which either may constitute either portions not covered by the specimen or portions which were skipped during scanning, for whatever reason.

Light gray areas 202 are indicative of a single relatively rapid scanning of the areas so shaded, and if such light gray areas are of a large percentage of the total scanning, it is further indicative of insufficient overlap in the screening and relatively short times spent on slide review. The darker gray areas 203 are indicative of overlap and greater periods of time spent in reviewing slide areas and black areas 204 are indicative of double overlap and extensive review of the areas so blackened. If areas within the blackened portions are designated with numbers of interest, it can be determined that the extensive time spent with such areas is because of possible anomalies therein.

As shown on screen 9, designated icons (i.e. +, ◊, ×, □, ⊙) which are enterable during scanning, are used to mark, via keyboard 12, positions of the computer correlated specimen, having such observed conditions (designated as POS, DYSP, ATYP, GLND, MORG, respectively). Toggle screen image 9a, just depicts such areas of interest, apart from the scanning history information of FIG. 3a in grayscale form. An initial setup screen (not shown) permits selection of various scanning parameters including correlative grayscale and dwell time conditions.

It is understood that the above description, drawings and examples are merely illustrative of the present invention and that changes in procedure and components may be made without departing from the scope of the present invention as defined in the following claims.

What is claimed is:

1. A specimen encoder device, for use during examination and subsequent review of the examination, of a specimen with one or more microscopes, wherein during said examination and review of examination, said specimen is movably mounted relative to a viewing lens of one of the microscopes; whereby the specimen is movable in an x-y direction plane, during said examination and review of examination;

the encoder device comprising computer and a viewing screen, and:

a. correlation means for translating movement of the specimen, in the x-y direction plane, to retrievable corresponding computer pixel locations and cursor movement on said viewing screen within a computer generated framed area diagram which correlatively contains the specimen;

b. means for marking microscope viewing areas, which are viewed during said examination, as correlated to the computer pixel locations, on the viewing screen and within the computer generated framed area diagram, with computer generated marking indicia;

c. means for recognizably varying the computer generated marking indicia, corresponding to specifically viewed microscope viewing areas, as a function of the period of time which was spent viewing each of said viewing areas and/or as a function of the number of times each, or a portion of each, of said viewing areas has been viewed.

2. The device of claim 1, wherein said device further comprises means for tagging, with predetermined symbols, areas of the viewing screen, correlating to areas of the specimen which are of interest for subsequent review.

3. The device of claim 2, wherein said means for tagging further provides an indication of the degree of relative interest and/or type of interest.

4. The device of claim 3, wherein said device further comprises means for viewing the tagging symbols, separate from said marking indicia.

5. The device of claim 1, wherein said means for recognizably varying the computer generated marking indicia, further comprises means for recognizably varying portions of the marked indicia, corresponding to a selected viewed viewing area, as a function of distance from the center of the selected viewed viewing area.

6. The device of claim 5, wherein said marking indicia comprises shading on a gray scale, having predetermined shading variations of gray, ranging from white to black; wherein said predetermined variations in shades of gray, are correlated to:

a. preselected amounts of time spent in viewing a microscope viewing area;

b. the number of times a viewing area, or portion thereof, was viewed; or c. the distance a portion of a viewing area is relative to the center of the viewing area; and d. combinations of the preselected amounts of time, number of times and distance.

7. A specimen encoder device, for use during examination and subsequent review of the examination, of a specimen with a microscope, wherein during said examination and review of examination, said specimen is movably mounted relative to a viewing lens of the microscope; whereby the specimen is movable in an x-y direction plane, during said examination and review of examination;

the encoder device comprising a computer, and:

a. correlation means for translating movement of the specimen, in the x-y direction plane, to retrievable corresponding computer pixel locations;

b. means for determining the area of the specimen viewed with the microscope during said examination, relative to the total area of the specimen viewable by the microscope, and as a function of time spent viewing the area of the specimen.

8. A specimen encoder device for use during examination and subsequent review of the examination, of a specimen with a microscope, wherein during said examination and review of examination, said specimen is movably mounted relative to a viewing lens of the microscope; whereby the specimen is movable in an x-y direction plane, during said examination and review of examination;

the encoder device comprising a computer, and:

a. correlation means for translating movement of the specimen, in the x-y direction plane, to retrievable corresponding computer pixel locations;

b. means for determining the area of the specimen viewed with the microscope during said examination, relative to the total area of the specimen viewable by the microscope, and as a function of time spent viewing the area of the specimen, wherein said device further comprises means for keeping track of time spent between movements of the specimen, $\Delta t$, while also maintaining an elapsed time $t_{total}$, whereby with each time the specimen is moved, $\Delta t$ is added to $t_{total}$ unless $\Delta t$ is greater than $t_{interruption}$, a pre-set time constant, wherein with an elapsed time of non-motion of at least $t_{interruption}$, $\Delta t$ is reset to zero, whereby, $t_{total}$ is the actual total time spent examining the specimen, less interruption times, which are at least equal to the pre-set time constant, $t_{interruption}$.

9. A specimen encoder device for use during examination and subsequent review of the examination, of a specimen with a microscope, wherein during said examination and review of examination, said specimen is movably mounted relative to a viewing lens of the microscope; whereby the specimen is movable in an x-y direction plane, during said examination and review of examination;

the encoder device comprising a computer, and:

a. correlation means for translating movement of the specimen, in the x-y direction plane, to retrievable corresponding computer pixel locations;

b. means for determining the area of the specimen viewed with the microscope during said examination, relative to the total area of the specimen viewable by the microscope, and as a function of time spent viewing the area of the specimen, wherein said device further comprises means for measuring the distance between first and second selected separate points on a specimen being viewed with the microscope, said means comprising means for recordation of the x-y coordinates of the first point when it is visible at a center of the microscope's field of view and the x-y coordinates of the second point when it is visible at the center of the microscope's field of view, and means for calculation of the distance between the recorded first and second points.

10. A specimen encoder device for use during examination and subsequent review of the examination, of a specimen with a microscope, wherein during said examination and review of examination, said specimen is movably mounted relative to a viewing lens of the microscope; whereby the specimen is movable in an x-y direction plane, during said examination and review of examination;

the encoder device comprising a computer, and:

a. correlation means for translating movement of the specimen, in the x-y direction plane, to retrievable corresponding computer pixel locations;

b. means for determining the area of the specimen viewed with the microscope during said examination, relative to the total area of the specimen viewable by the microscope, and as a function of time spent viewing the area of the specimen, wherein said device further comprises means for measuring a predefined area, said area being defined by line segments of a polygon which encloses the specimen whose area is to be determined, wherein said line segments and the polygon formed thereby, are defined by recordation of the x-y coordinates, at a center of the view of the microscope viewing area, of sufficient points at the edge of the predefined area, which are connected to provide said line segments and the polygon, said device further including means for calculation of the area enclosed by said polygon.

11. A specimen encoder device, for use during examination and subsequent review of the examination, of a specimen with a microscope, wherein during said examination and review of examination, said specimen is movably mounted relative to a viewing lens of the microscope; whereby the specimen is movable in an x-y direction plane, during said examination and review of examination;

the encoder device comprising a computer, and:
a. correlation means for translating movement of the specimen, in the x-y direction plane, to retrievable corresponding computer pixel locations;
b. means for determining the area viewed at least twice during said examination, relative to the total area of the specimen viewed with the microscope during said examination, and as a function of time spent viewing the area viewed.

* * * * *